(12) United States Patent
Ferri et al.

(10) Patent No.: US 8,146,445 B2
(45) Date of Patent: Apr. 3, 2012

(54) EXTRACTIVE PROBE FOR HOT FLUE GAS AND PROCESS MEASUREMENT

(75) Inventors: Nicholas William Ferri, Apex, NC (US); Antonio Volpicelli, Upton, MA (US)

(73) Assignee: Delta Measurement and Combustion Controls, LLC, Hopedale, MA (US)

( * ) Notice: Subject to any disclaimer, the term of this patent is extended or adjusted under 35 U.S.C. 154(b) by 485 days.

(21) Appl. No.: 12/390,025

(22) Filed: Feb. 20, 2009

(65) Prior Publication Data

US 2009/0211370 A1    Aug. 27, 2009

Related U.S. Application Data

(60) Provisional application No. 61/031,133, filed on Feb. 25, 2008.

(51) Int. Cl.
*G01N 1/22* (2006.01)

(52) U.S. Cl. .................................. 73/863.23; 73/863.83

(58) Field of Classification Search .. 73/863.81–863.83, 73/863.85, 863.51, 863.54, 863.23–863.25, 73/863.03, 863.41, 864.34, 864.73
See application file for complete search history.

(56) References Cited

U.S. PATENT DOCUMENTS

| | | | |
|---|---|---|---|
| 3,960,500 A | 6/1976 | Ross et al. | |
| 4,485,684 A | 12/1984 | Weber et al. | |
| 4,653,334 A | 3/1987 | Capone | |
| 4,912,985 A | 4/1990 | Daum et al. | |
| 5,596,154 A | 1/1997 | Baughman | |
| 5,824,919 A | 10/1998 | Hansen | |
| 6,675,664 B1 * | 1/2004 | Lilienthal et al. | 73/863.23 |
| 7,337,683 B2 | 3/2008 | DeFriez et al. | |
| 2002/0166365 A1 | 11/2002 | Kogure et al. | |
| 2008/0078260 A1 | 4/2008 | Johnston et al. | |
| 2008/0148871 A1 | 6/2008 | Himes et al. | |

FOREIGN PATENT DOCUMENTS

JP    63-63937    *  3/1988

* cited by examiner

*Primary Examiner* — Robert R Raevis
(74) *Attorney, Agent, or Firm* — Murphy, Bilak & Homiller, PLLC (57) ABSTRACT

Methods and apparatus for extracting gas samples from a particle-laden fluid stream are disclosed. An exemplary sampling probe apparatus includes a probe head having an upstream face and a downstream face, an intake orifice inwardly tapering from the upstream face into a central bore region of a cavity within the probe head, and an outlet orifice outwardly tapering from said central bore region to the downstream face, so as to permit fluid gas flow through the central bore region of the cavity. A filter device disposed within the cavity of the probe head extends between the intake orifice and the outlet orifice so as to divide a low-pressure sampling region of the cavity from the central bore region. A sampling tube in fluid communication with the low-pressure sampling region provides for extracting gas samples from the low-pressure sampling region of the cavity.

16 Claims, 8 Drawing Sheets

EXTRACTIVE PROBE FOR HOT FLUE GAS AND PROCESS MEASUREMENT

RELATED APPLICATION

This application claims priority under 35 U.S.C. §119(e) to U.S. Provisional Patent Application Ser. No. 61/031,133, filed Feb. 25, 2008 and titled "Venturi/Vortex extractive probe for use on Hot Flue Gas and Process Measurement," the entire contents of which are incorporated by reference herein.

TECHNICAL FIELD

The present invention relates generally to methods and apparatus for extracting gas samples from a particle-laden gas stream.

BACKGROUND

Various techniques and equipment have been developed to ensure efficient and clean operation of burners used in power generation, industrial, commercial, and residential furnaces, heat treating ovens, and boilers. These techniques include the use of sampling probes that are inserted into a flue or other pipe or duct and configured to extract a sample of flowing gas for analysis, such as for measurement of carbon monoxide levels.

In applications where the gas stream contains particulate matter, the gas is typically filtered at the sampling point, to prevent the particles from reaching the analysis point. Various filters, including sintered metal filters, have been used for this purpose. However, it is well known that these filters can become clogged and must be periodically cleaned, preferably without removing the probe from service. To address this problem, various methods for purging the filters have been developed. In many cases, a sampling tube, which normally carries a sample of the gas to an analysis unit, is pressurized, to force air through the probe in a reverse direction, thus cleaning the filter. One problem with this approach is that moisture in the sampling line is forced through the filter and probe head. This moisture can combine with the gas particles to clog the filter and/or other parts of the probe. Accordingly, improved techniques and devices for extracting gas samples from a particle-laden fluid stream are needed.

SUMMARY

Disclosed herein are methods and apparatus for extracting gas samples from a particle-laden gas stream. In an exemplary embodiment, a sampling probe apparatus includes a probe head having an upstream face and a downstream face, an intake orifice extending from the upstream face to a first opening into a central bore region of a cavity within the probe head, and an outlet orifice extending from a second opening out of said central bore region to the downstream face, so as to permit fluid gas flow through the central bore region of the cavity. In several embodiments, the inlet orifice is inwardly tapered from the upstream face to the first opening, and the outlet orifice may also be outwardly tapered between the second opening and the downstream face; this arrangement induces Venturi acceleration of the gas flowing into and through the central bore region of the probe head cavity. A filter device is disposed within the cavity of the probe head and extends between the intake orifice and the outlet orifice so as to divide a low-pressure sampling region of the cavity from the central bore region. A sampling tube in fluid communication with the low-pressure sampling region provides for extracting gas samples from the low-pressure sampling region of the cavity.

In some embodiments, the filter device comprises a tubular filter element disposed between the intake and outlet orifices, so that the low-pressure sampling region comprises an annular void around the tubular filter element. In these and other embodiments, the tubular filter element may comprise a sintered alloy or ceramic filter. In some of these embodiments, the tubular filter element comprises an annular flange at one end or at each end of the filter element, with the annular flange having a contact surface for contacting an interior surface of the probe head. The contact surface may have a textured contact pattern, in some embodiments, such as a pattern comprising one or more annular ribs.

In several embodiments, the sampling probe apparatus further comprises a cantilever portion having first and second ends and attached to the probe head at the first end, with a flange attached to the cantilever portion at the second end and configured for mounting to a wall of a gas-carrying duct. In some of these embodiments, the sampling tube passes through the cantilever portion from the probe head to the flange. Several embodiments further comprise a purging tube in fluid communication with the low-pressure sampling region of the probe head cavity, for supplying pressurized air to the probe head. This purging tube may also pass through the cantilever portion, in some embodiments. In some embodiments, the purging tube is arranged so that it is substantially parallel to the sampling tube, in a plane that is substantially perpendicular to the flow of gas through the probe head.

An exemplary method for extracting gas samples from a fluid gas stream comprises diverting a portion of the fluid stream through a probe head positioned within a gas-carrying duct, the probe head having an intake orifice inwardly tapering from an upstream face of the probe head into a central bore region of a cavity within the probe head, and an outlet orifice outwardly tapering from said central bore region to a downstream face of the probe head, so as to permit fluid gas flow through the central bore region of the cavity. Gas samples are then extracted from a low-pressure region of the cavity divided from the central bore region of the cavity by a filter device disposed within the cavity and extending between the intake orifice and the outlet orifice, using a sampling tube in fluid communication with the low-pressure sampling region. In some embodiments, the method further comprises purging the filter device by supplying pressurized air to the low-pressure sampling region of the probe head through a purging tube in fluid communication with the low-pressure sampling region.

Of course, those skilled in the art will appreciate that the present invention is not limited to the above contexts or examples, and will recognize additional features and advantages upon reading the following detailed description and upon viewing the accompanying drawings.

DETAILED DESCRIPTION

As briefly discussed above, various techniques and devices are presently known for extracting gas samples from a fluid stream for analysis of the gas. However, the filters used in many of these systems are prone to clogging, and currently employed techniques for purging these filters are often inadequate. The probe heads disclosed herein address these problems in two ways. First, various embodiments of the probe heads disclosed herein reduce the load on the filter used to filter the gas sample by using venturi and/or vortex acceleration of the particles in the fluid stream to separate the particles from the sampled gas by means of kinetic energy. The increased particle speed tends to carry the particles past the probe head's integral filter, rather than into or through it. Second, these embodiments further exploit an in situ slipstream effect, extracting the gas samples from a low-pressure zone within the probe head. This extraction of the gas sample from the low-pressure zone of the probe head reduces the likelihood that particles are pulled into or through the filter, or into the sampling tube.

Figure 1:
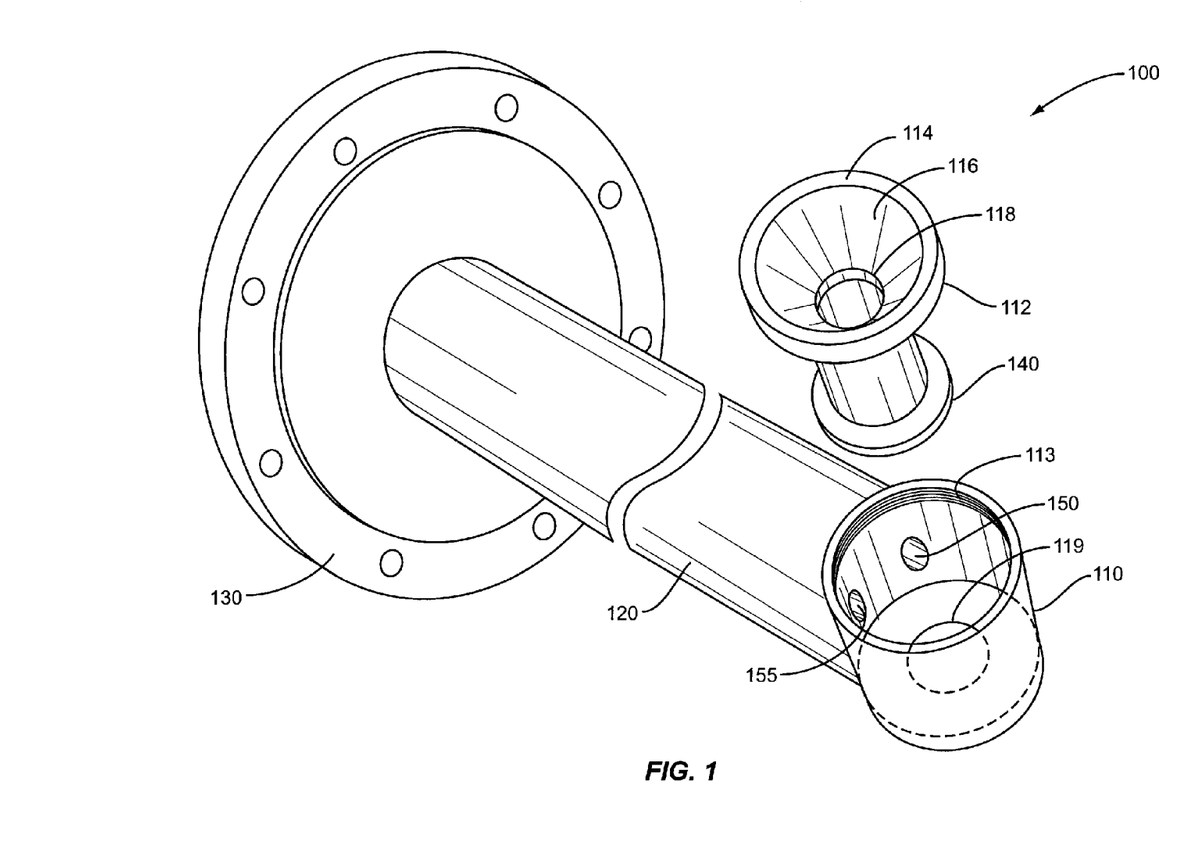
FIG. 1 is a perspective view of a partially disassembled extractive probe apparatus according to some embodiments of the present invention.

FIG. 1 illustrates a perspective view of a partially disassembled extractive probe 100 according to some embodiments of the invention. As shown in FIG. 1, the probe 100 includes a probe head body 110, from which a probe cap 112 has been removed by unscrewing the cap 112 from threads 113 formed inside probe head body 110. Probe head body 110 is attached to an extended probe cantilever 120, which is dimensioned for facilitating the placement of the probe head well into a fluid-carrying duct (e.g., a flue or chimney), and may be as long as 10 feet, or even longer. Cantilever portion 120 is in turn attached to a flange 130, for rigidly attaching the probe assembly to the wall of the duct.

The probe head of FIG. 1 includes a tapered input and output region, which cause venturi/vortex acceleration of the gas and particles. As shown in FIG. 1, the probe cap 112 includes a tapered region that defines an intake orifice 116 extending from the face 114 of the probe to an opening 118 at the base of the tapered region; when probe cap 112 is assembled onto probe head body 110, the intake orifice 116 empties into a cavity defined by the side walls of the probe head body 110, the probe cap 112, and the bottom of the probe head body 110. In the pictured embodiment, the bottom and side walls of the probe head body 110 form a single unit; in some embodiments the bottom of the probe head body 110 comprises another removable cap, similar to probe cap 112. In either case, the bottom of the probe head 110 comprises an outlet orifice 117 (not visible in FIG. 1) outwardly tapering from a second opening 119 from the cavity within the probe head to the bottom surface of the probe head (not shown).

Also shown in FIG. 1 is a tubular filter element 140, which is dimensioned to extend between the intake orifice 116 and outlet orifice 117 when the probe head is fully assembled. When the tubular filter element 140 and the probe cap 112 are installed, the filter element 140 is securely positioned within the cavity and divides a central bore region of the cavity, extending between the intake orifice 116 and outlet orifice 117, from an annular void outside the tubular filter but inside the side walls of probe head body 110.

When the probe head of FIG. 1 is installed in a fluid-carrying duct, venturi acceleration of the particle-laden gas stream as it passes into the probe head body 110 and through the central bore region of the cavity creates a relatively low-pressure zone in the cavity. Samples of the gas can thus be taken from a low-pressure sampling region that is within this low-pressure zone but outside the tubular filter element 140. As shown in FIG. 1, gas samples are extracted from the low-pressure sampling region via a sampling tube supplied through outlet 150. As will be discussed in further detail below, pressurized air may be supplied to the probe head through inlet 155, to purge the filter of contaminants.

The exemplary probe 100 of FIG. 1 is constructed from a high-temperature and abrasive-resistant alloy material. This alloy material may be of any type suitable for a particular installation, in view of the corrosive and eroding effects of the gas and particulate matter. Preferably, the material should be suitable for long-term application in an environment of continuous operation.

The tubular filter element 140 may comprise a sintered metal alloy or ceramic (e.g., silicon carbide) filter, in some embodiments. For instance, the alloy may be a corrosion-resistant alloy such as a member of the Hastelloy® family of alloys from Haynes International, Inc. In some embodiments of the invention, the probe filter serves a dual purpose. First, the porosity of the probe filter may be selected to be finer than most particles in the gas stream, to minimize particle migration into the sample tube. Second, the porosity may be fine enough to create back pressure during a purge cycle, so that at least a portion of the pressurized air supplied by the purging tube may be forced back through the sampling tube. The porosity of the filter may thus vary, depending on the particular application. For example, the filter element 140 may be configured to filter particles as small as ½ to 2 microns in a system employed to monitor carbon monoxide levels in a coal combustion flue.

Figure 5:
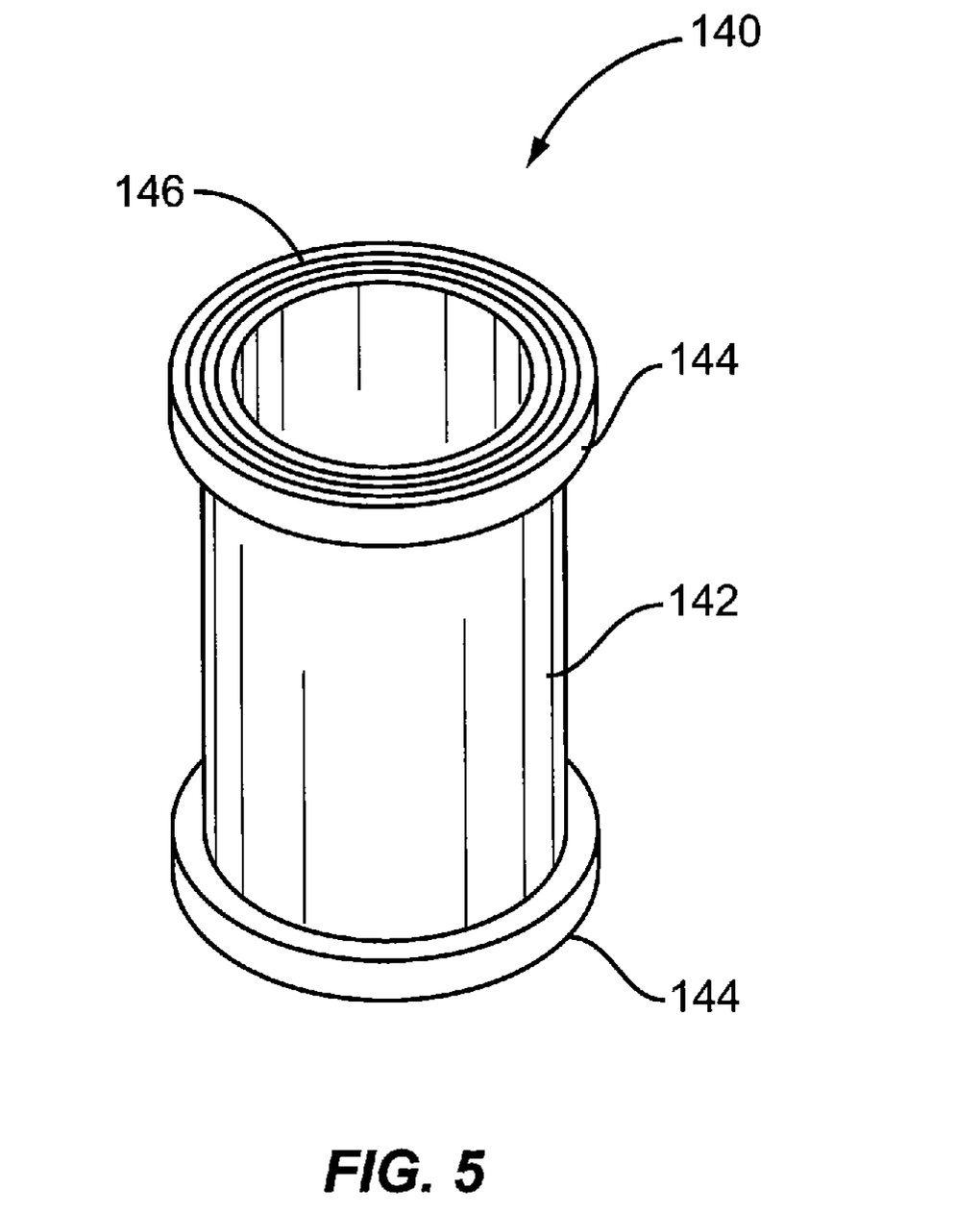
FIG. 5 illustrates an exemplary tubular filter element according to some embodiments of the invention.

An exemplary filter element 140 is pictured in FIG. 5; in this embodiment filter element 140 comprises a porous central tube section 142, and an annular flange 144 at each end. The outer surfaces of the flanges 144 are contact surfaces for contacting an interior surface of the probe head, and in some embodiments may comprise a textured contact pattern, to provide a better seal between the filter and probe body. For example, the filter element 140 of FIG. 5 includes several annular ribs 146 on the contact surface; these ribs help to prevent particles from leaking around the filter into the low-pressure sampling region. Of course, those skilled in the art will recognize that other textured contact patterns are possible, such as a crosshatch pattern.

Purging, which in the probe 100 of FIG. 1 is accomplished by supplying pressurized air to the probe head body through outlet 155, via a purging tube that is separate from the sampling tube, also serves a dual purpose. First, the purging operation cleans filter element 140, as the pressurized air is forced through the filter element from the low-pressure sampling region into the central bore region of the probe head cavity. Second, the purging operation removes moisture and particulate matter from the sample line. Because the probe head and sintered filter is pressurized from a source separate from the sampling tube, moisture and particulate matter is driven back through the sampling tube and towards a moisture trap/drain (not shown) for removal. As a result of this configuration, particulate matter and moisture in the sampling tube is not driven back to the high-temperature probe head, where plugging of the sintered filter might otherwise occur.

In some embodiments, the purging process may be a two phase process. In one phase, a valve attached to the sampling tube is opened so that air may flow from the probe head, through the sampling tube, and into the moisture trap and drain. Because of back pressure exerted by the filter element, at least a portion of the pressurized air supplied to the probe head through the purging tube flows through the sampling tube, removing moisture and particulate matter from the sampling tube. In a second phase, the valve is closed—in this phase the pressurized air is forced through the filter element, removing embedded particles from the filter element 140 and forcing the particles back into the gas stream to be swept away. Those skilled in the will note that the sampling tube and purging tube inlets to the probe head of FIG. 1 are side-by-side, and offset from the center of the probe head. Although other arrangements are possible, this arrangement encourages the flow of purging air around the outer surface of the filter element during the purging process, facilitating a more even and thorough cleaning of the filter.

Figure 2:
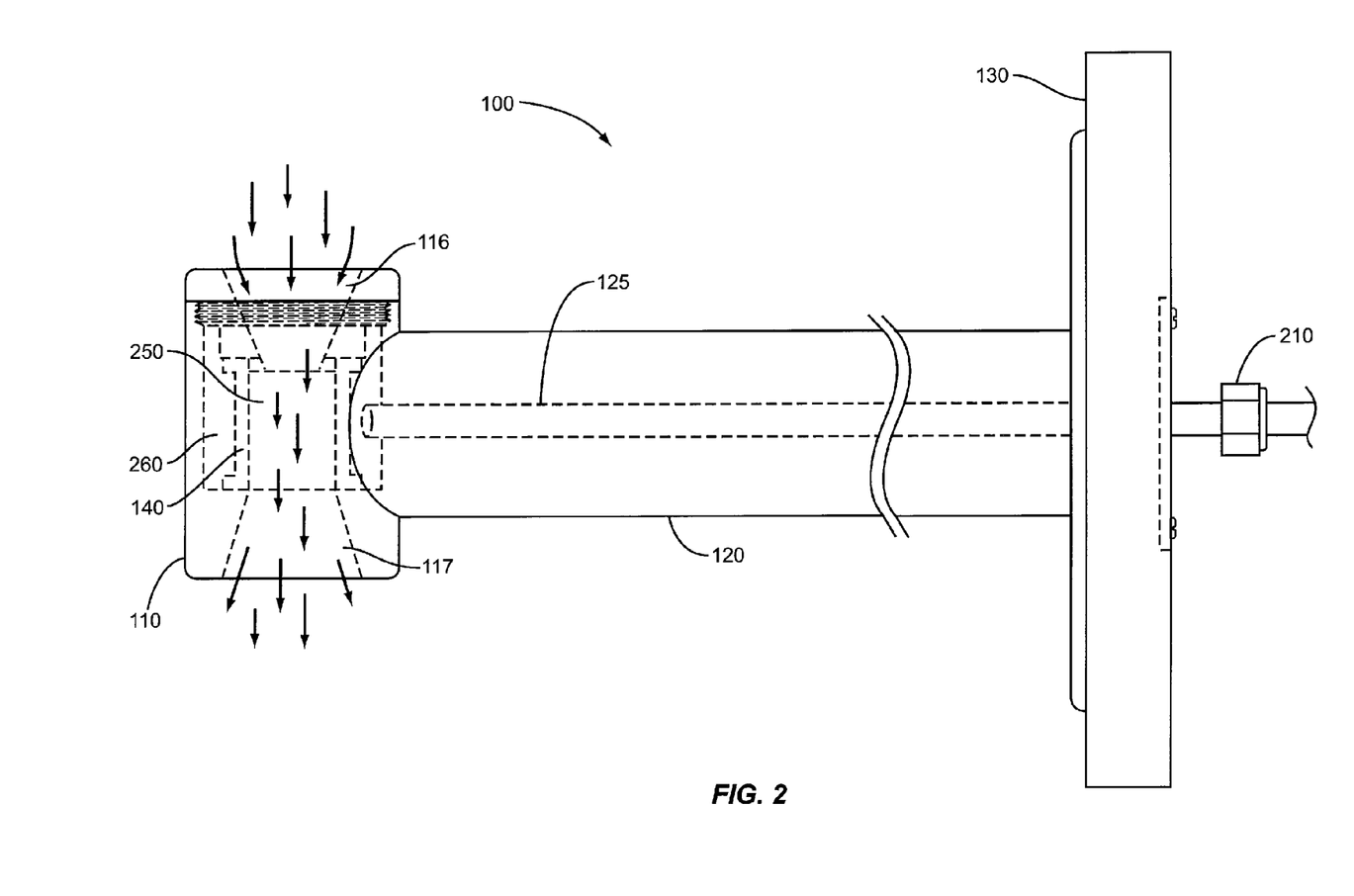
FIG. 2 is a side view of the extractive probe apparatus of FIG. 1.

FIG. 2 provides a side view of the extractive probe apparatus of FIG. 1. In this view, gas flows from the top to bottom. Process gas flows through the head, where a venturi and/or vortex effect causes the gas stream to speed up as it passes through the intake orifice 116 into the central bore region 250 of the probe head's internal cavity. In some cases, the surface of the tapered intake orifice 116 may comprise one or more grooves spiraling around the orifice, to impart a rotational "vortex" flow to the gas flowing into and through the probe head. The increased momentum of the accelerated particles reduces the ability of the sample gas suction to pull particles through the tubular filter element 140 into the sampling tube 125, which passes through the cantilever portion 120 and flange 130 to a coupler 210. In addition, the venturi effect caused by the acceleration of the process gas through the narrowed throat formed by intake outlet 116 and outlet orifice 117 creates a low-pressure sampling region 260 surrounding the filter 140, thus allowing for gas suction into the sampling tube with reduced interaction with particles. The increased axial flow through the central bore region 250 generates a reduced static pressure typical of an aspirator, and at suitable velocity will generate a vacuum reference from the low-pressure sampling region 260 to the central bore region 250. At the same time, the vortex effect will create low pressure in the central bore region 250, relative to the filter 140 and the annular sampling region 260; this will encourage "roping" of the particles flowing through the probe head in the center of the central bore region, further reducing the likelihood that particles are drawn into the filter 240.

Figure 3:
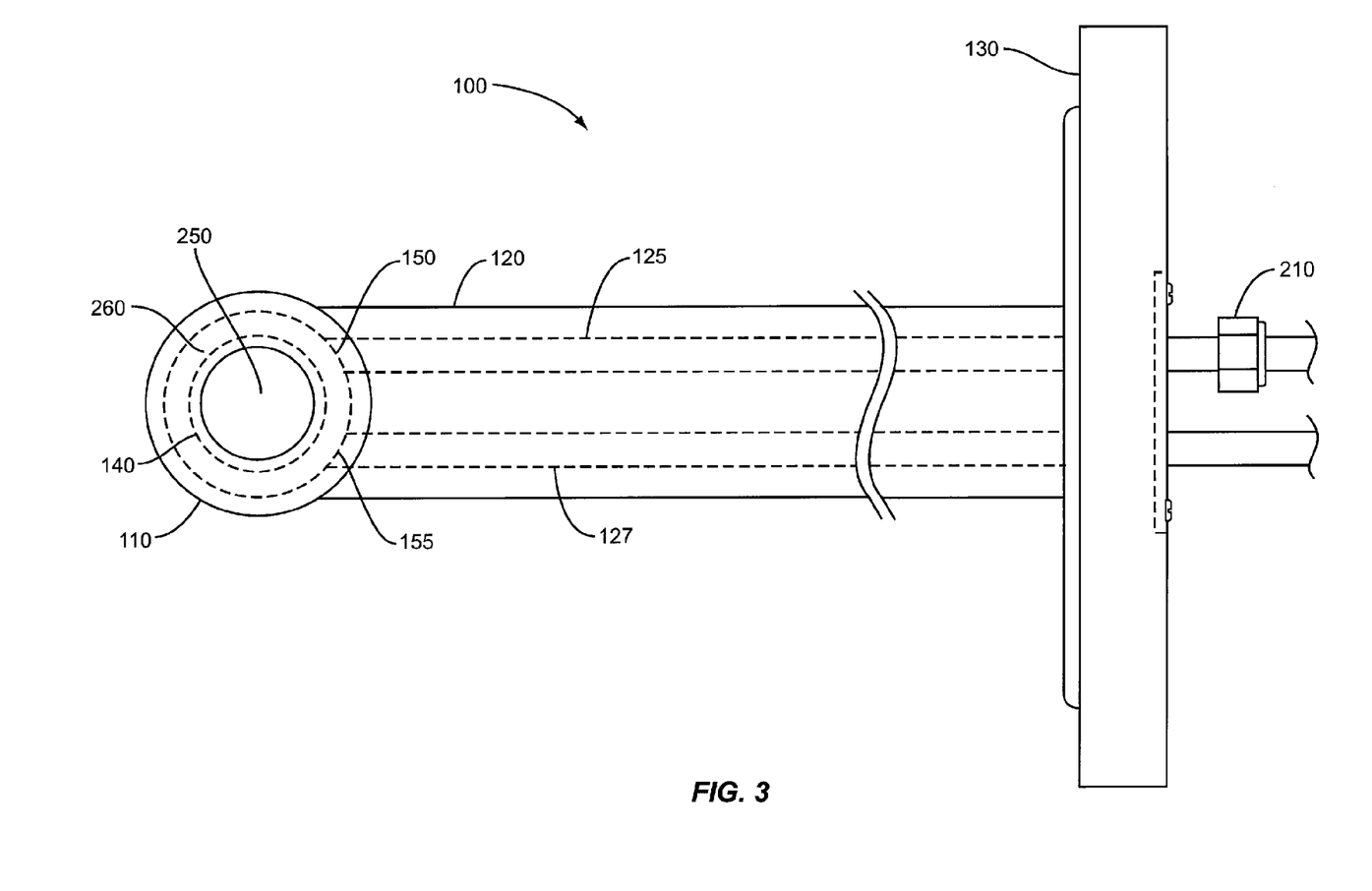
FIG. 3 is a top view of the extractive probe apparatus of FIG. 1.

FIG. 3 provides an overhead illustration of the exemplary probe apparatus of FIGS. 1 and 2. In this view, the separate sampling tube 125 and purging tube 127 are more clearly seen. As discussed above, the purge tubing 127 is separately tapped into the low-pressure sampling region 260 of the probe head, via opening 155, to provide more effective cleaning of the sintered filter element 140 and the sampling tube 125. Purging air forced into the probe head body 110 through the purging tube 127 simultaneously cleans the pores of the sintered filter 140, and blows any additional material, debris, and moisture in the sampling tube 125 back towards an external analyzer drain (not shown) for removal. Debris and moisture are thus never forced out of the analyzer into the probe head body 110 or hot sampling tubing.

Figure 4:
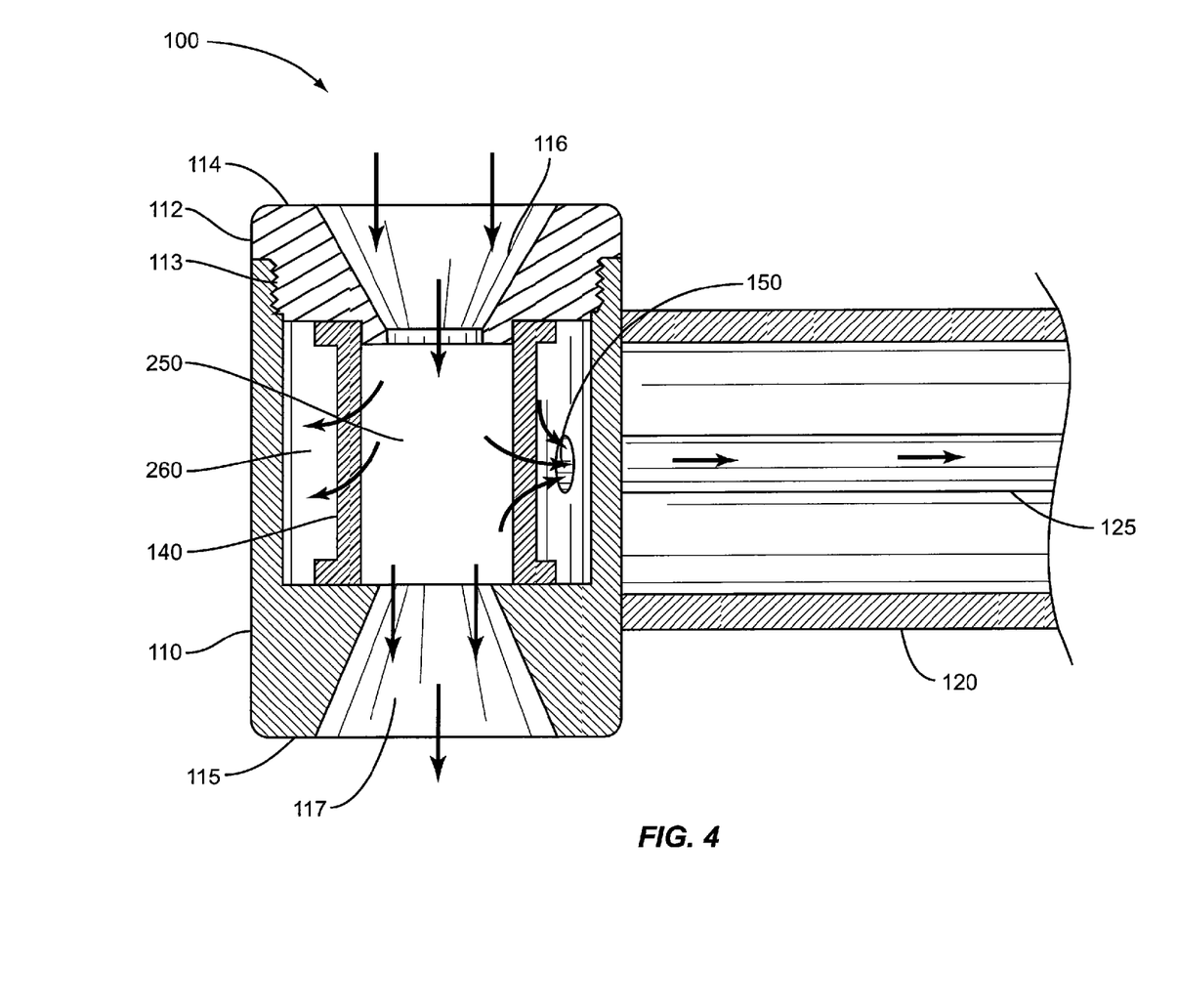
FIG. 4 provides a cross section view of the probe apparatus of FIG. 1.

FIG. 4 provides a cross-sectional view along a central line of the probe head body 110. Again, process gas flows from the top to bottom. Accordingly, a portion of the process gas flow impinges upon the upstream face 114 of the probe head, and flows through the inwardly tapering intake orifice 116 into a central bore region 250 of the cavity within the probe head body 110, emerging through an outwardly tapering outlet orifice 117 extending between the central bore region 250 and the downstream face 115 of the probe head. The central bore region 250 is generally defined by the theoretical column between the narrowest portions of the intake orifice 116 and outlet orifice 117, and is the region of the probe head's internal cavity through which the majority of the accelerated fluid stream flows through the probe head. Those skilled in the art will appreciate that the venturi effect from the accelerated fluid flow through the probe head creates a low-pressure zone within the probe head 110; the tubular filter element is disposed within this low-pressure zone and extends from the inner ends of intake orifice 116 and outlet orifice 117, dividing the central bore region 250 of the probe head cavity from an annular low-pressure sampling region 260. The sampling tube 150 is in fluid communication with the low-pressure sampling region 260 through inlet 150, and passes through cantilever portion 120 to an external analyzer. The cantilever portion may include thermal insulation (not shown) surrounding all or part of the purging and/or sampling tubes, in some embodiments, to reduce temperature changes in the sampled gas and reduce condensation, which can interact with residual particles and plug the tubes and/or connecting fittings.

Figure 6:
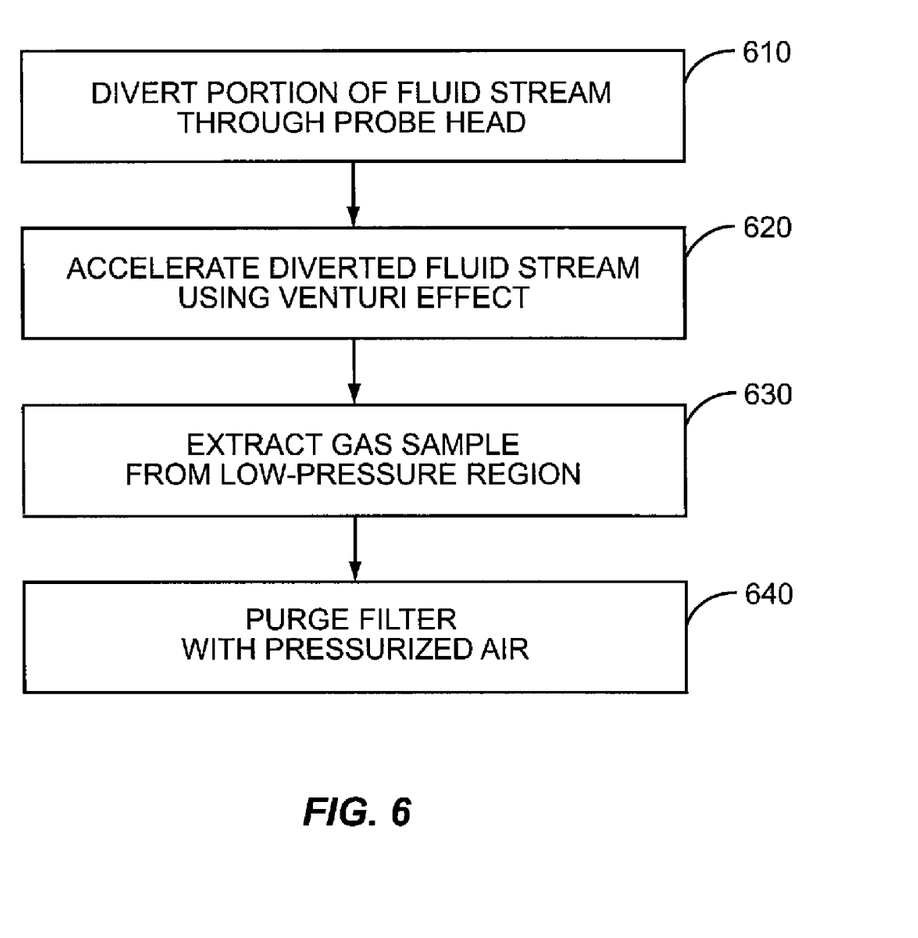
FIG. 6 is a process flow diagram illustrating an exemplary method for extracting gas samples from a particle-laden gas stream for analysis.

With the above-described probe apparatus configurations in mind, those skilled in the art will appreciate that FIG. 6 illustrates a general method for extracting gas samples from a particle-laden fluid stream. The process illustrated in FIG. 6 begins, as shown at block 610, with the diversion of a portion of the fluid stream through a probe head positioned within a gas-carrying duct. As described above, the probe head has an intake orifice inwardly tapering from an upstream face of the probe head into a central bore region of a cavity within the probe head, and an outlet orifice outwardly tapering from said central bore region to a downstream face of the probe head, so as to permit fluid gas flow through the central bore region of the cavity. As a result of this configuration, the fluid flow through the central bore region of the probe head cavity is accelerated, as shown at block 620, and a low-pressure region created within the cavity of the probe head. As shown at block 630, a gas sample is extracted from this low-pressure region, through a filter device disposed within the cavity and extending between the intake orifice and the outlet orifice, using a sampling tube in fluid communication with the low-pressure sampling region of the cavity. Finally, as shown at block 640, the filter device is periodically purged by supplying pressurized air to the low-pressure sampling region of the probe head through a purging tube in fluid communication with the low-pressure sampling region of the probe head cavity.

Those skilled in the art will recognize that a number of variations of the techniques described above and the basic probe configuration illustrated in FIGS. 1-4 are possible. For instance, although the probe body 110 in FIGS. 1-4 is cylindrical, as are the tubular filter element 140 and the central bore region 250 between the tapered orifices 116 and 117, other shapes for each are possible. For example, an alternative configuration might have a box-shaped probe head body, and or a filter element with a rectangular interior bore. Likewise, although the configuration of FIGS. 1-4 includes an annular low-pressure sampling region that completely surrounds the tubular filter element 140, other embodiments might have a low-pressure sampling region around only part of the central bore region 250. In some of these embodiments, the filter element need not surround the entire central bore region of the cavity within the probe head, provided simply that it extends between the intake orifice and the outlet orifice so as to divide a low-press sampling region of the cavity from the central bore region.

As discussed earlier, the surface of the inlet orifice may include one or more spiral grooves, to induce or increase a rotational vortex flow to the gas flowing through the probe head. Some embodiments may include these spiral grooves on the surface of the outlet orifice as well. Furthermore, the embodiments pictured in FIGS. 1-4 have an outlet orifice extending from an opening 119 into the interior cavity that is larger than the corresponding opening 118 from the inlet orifice to the interior cavity. This approach allows expansion of the sample gas upon exit and reduces collisions between particles as they flow through the interior cavity. However, other embodiments may have openings of identical size, or an inlet opening that is larger than the outlet opening, although the latter approach may increase the possibility that particles become lodged at or near the outlet opening or leak around the bottom of the filter element into the low-pressure sampling region.

Figure 7:
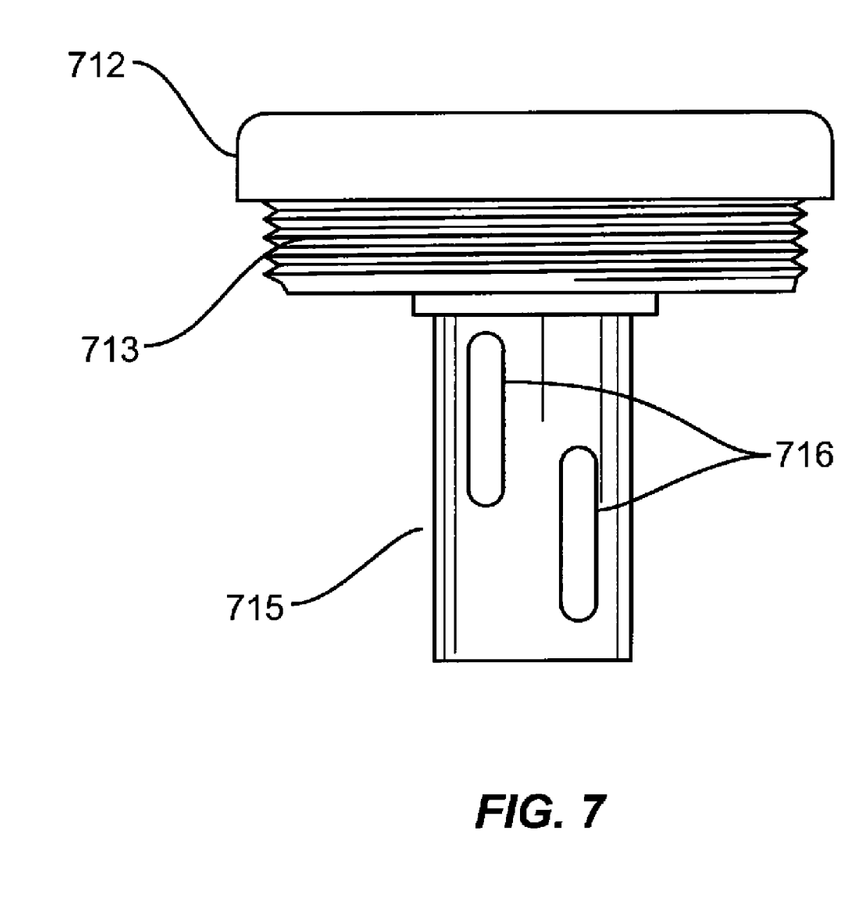
FIG. 7 illustrates an exemplary probe cap according to some embodiments of the invention.
Figure 8:
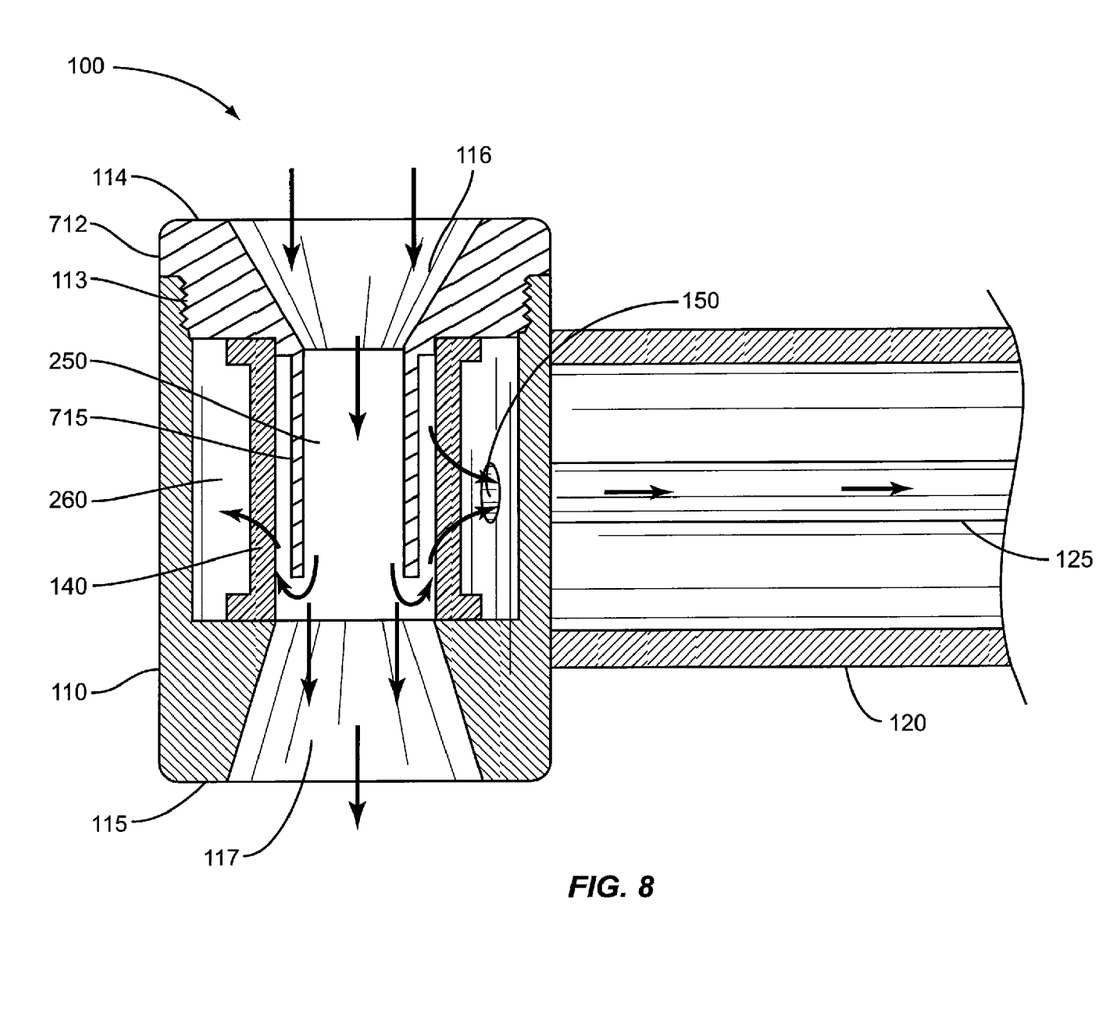
FIG. 8 illustrates a cross section view of a probe apparatus that includes the probe cap of FIG. 7.

A probe cap 712 according to still another embodiment of an extractive sampling probe 100 is pictured in FIG. 7. Like probe cap 112 of FIG. 4, probe cap 712 comprises a tapered inlet orifice 116, and is threaded with threads 713 so that it may be installed into probe head body 110, as shown in FIG. 8. Unlike probe cap 112, however, probe cap 712 also comprises an extended dust shield 715. In the pictured embodiment, the dust shield 715 is a hollow cylinder that extends through a substantial portion of the sintered filter 140.

The probe head configuration illustrated in FIG. 8, with dust shield 715 extending through the central bore region of the probe head, prevents flowing ash and air that enters the intake orifice 116 at an angle from directly impacting the inside face of the sintered filter 140. The impact of ash on the sinter can have an abrasion effect, which can cause a section of the filter to plug and increase our pressure drop across the filter. As shown in FIG. 8, a small gap, e.g., 0.10 to 0.50 inches, is maintained between the dust shield 715 and the inner face of the sintered filter. In some embodiments, one or more holes or slits 716 may be formed in the dust shield 715, providing for somewhat increased interaction between the central bore region of the probe head and the low pressure sampling region 260 around the sintered filter 140. In any event, just as negative pressure was created in the throat of the venturi in the probe head 100 of FIG. 4, so will negative pressure be derived at the end of the dust guard 715 in the embodiment pictured in FIG. 8. This will help keep the opening clear, along with the use of purging cycles.

Still other embodiments may comprise minimal tapering of the inlet and outlet orifices, in contrast to the distinct tapering illustrated in FIGS. 1-4 and in FIG. 8. Indeed, some embodiments may have no tapering at all on one or both of the orifices; although these embodiments will have little or no Venturi acceleration of the gases, they will nonetheless benefit from the inertial tendency of the particles to flow past the filter rather than through it, and may also benefit from the inventive arrangement of sampling and purging tubes disclosed herein. Finally, although the embodiment of FIGS. 1-4 and FIG. 8 includes a sampling tube 125 and a purging tube 127 passing inside and through the cantilever portion 120 to flange 130, other configurations might have one or both of these tubes separate from and/or outside of a supporting member for the probe head.

Indeed, as the previous discussion suggests, the present invention may be carried out in still other specific ways than those set forth without departing from the scope of the inventive techniques illustrated by the specific embodiments illustrated herein. Thus, the present invention is not limited to the features and advantages detailed in the foregoing description, nor is it limited by the accompanying drawings. Instead, the present invention is limited only by the following claims and their legal equivalents.

What is claimed is:

1. A sampling probe apparatus for extracting gas samples from a fluid stream, comprising:
   a probe head having an upstream face and a downstream face, an inwardly tapered intake orifice extending from the upstream face to a first opening into a central bore region of a cavity within the probe head, and an outlet orifice extending from a second opening out of said central bore region to the downstream face, so as to permit fluid gas flow through the central bore region of the cavity;
   a tubular filter device disposed within the cavity and extending between the intake orifice and the outlet orifice, with a longitudinal axis of the tubular filter device extending from the intake orifice to the outlet orifice, so as to divide a low-pressure sampling region of the cavity from the central bore region; and
   a sampling tube, in fluid communication with the low-pressure sampling region, for extracting gas samples from the low-pressure sampling region of the cavity.

2. The sampling probe apparatus of claim 1, wherein the outlet orifice outwardly tapers from the second opening to the downstream face.

3. The sampling probe apparatus of claim 1, wherein the second opening is larger than the first opening.

4. The sampling probe apparatus of claim 1, wherein the intake orifice comprises one or more spiral surface grooves for imparting vortex rotation to a portion of the fluid gas flow through the central bore region of the cavity.

5. The sampling probe apparatus of claim 1, further comprising a purging tube in fluid communication with the low-pressure sampling region for supplying pressurized air to the low-pressure sampling region of the cavity.

6. The sampling probe apparatus of claim 5, wherein the purging tube and sampling tube are disposed substantially parallel to one another in a plane substantially perpendicular to the gas flow through the central bore region of the cavity.

7. The sampling probe apparatus of claim 1, wherein the tubular filter device comprises a cylindrical tubular filter element disposed between the intake and outlet orifices and wherein the low-pressure sampling region comprises an annular void around the cylindrical tubular filter element.

8. The sampling probe apparatus of claim 7, wherein the tubular filter element comprises a sintered alloy filter.

9. The sampling probe apparatus of claim 7, wherein the tubular filter element comprises a ceramic filter.

10. The sampling apparatus of claim 7, wherein the tubular filter device includes an annular flange disposed at an end of the tubular filter element and having a contact surface configured for contacting an interior surface of the probe head.

11. The sampling apparatus of claim 10, wherein the contact surface of the annular flange comprises a textured contact pattern.

12. The sampling apparatus of claim 11, wherein the textured contact pattern comprises one or more annular ribs on the contact surface of the annular flange.

13. The sampling probe apparatus of claim 1, further comprising:
   a cantilever portion having first and second ends and attached to the probe head at the first end; and
   a flange attached to the cantilever portion at the second end and configured for mounting to a fluid-carrying duct;

wherein the sampling tube passes through the cantilever portion from the probe head to the flange.

14. A method for extracting gas samples from a fluid stream, comprising:

diverting a portion of the fluid stream through a probe head positioned within a fluid-carrying duct, the probe head having an intake orifice inwardly tapering from an upstream face of the probe head into a central bore region of a cavity within the probe head, and an outlet orifice outwardly tapering from said central bore region to a downstream face of the probe head, so as to permit fluid gas flow through the central bore region of the cavity; and extracting the gas samples from a low-pressure region of the cavity divided from the central bore region of the cavity by a filter device disposed within the cavity and extending between the intake orifice and the outlet orifice, using a sampling tube in fluid communication with the low-pressure sampling region.

15. The method of claim 14, further comprising purging the filter device by supplying pressurized air to the low-pressure sampling region of the probe head through a purging tube in fluid communication with the low-pressure sampling region.

16. The method of claim 15, wherein the purging tube for supplying pressurized air to the low-pressure sampling region of the probe head is separate from the sampling tube.

* * * * *